Figure 1:
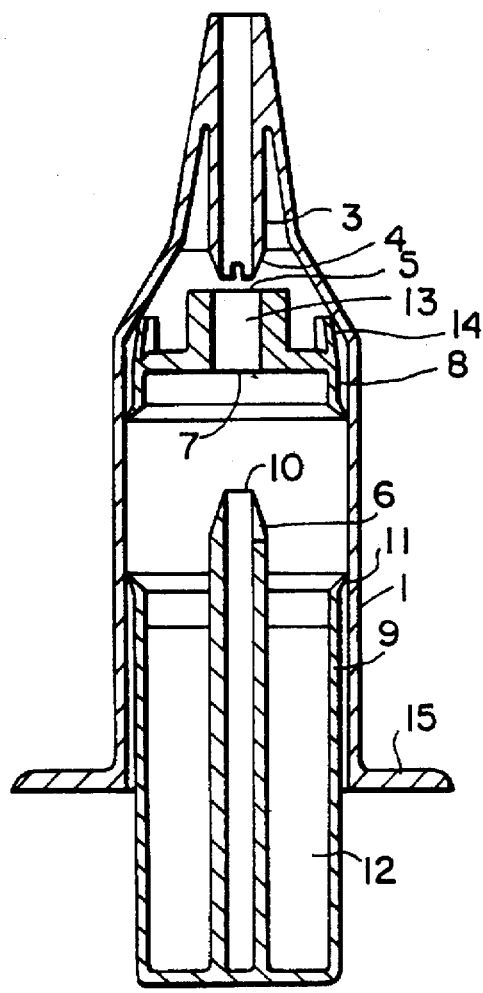

United States Patent [19]

Elk et al.

[11] Patent Number: 5,683,361

[45] Date of Patent: Nov. 4, 1997

[54] DISPOSABLE DISPENSER FOR POWDER

[75] Inventors: Svend Elk, Birkeroed; Kim Steengaard, Hvidovre; Hans Köster, Hellerup, all of Denmark

[73] Assignee: Novo Nordisk A/S, Bagsvaerd, Denmark

[21] Appl. No.: 221,286

[22] Filed: Mar. 31, 1994

Related U.S. Application Data

[63] Continuation of Ser. No. 900,027, Jun. 17, 1992, abandoned.

[30] Foreign Application Priority Data

Dec. 10, 1991 [DK] Denmark .................. 1985/91

[51] Int. Cl.⁶ .................................. A61M 13/00
[52] U.S. Cl. .................. 604/58; 604/94; 604/200; 222/82
[58] Field of Search .................. 604/57–60, 94, 604/173, 200, 244, 253; 222/82, 83, 631–634

[56] References Cited

U.S. PATENT DOCUMENTS

| | | | |
|---|---|---|---|
| 2,151,418 | 3/1939 | Bolté | 604/58 |
| 2,307,986 | 1/1943 | Bolte et al. | 128/266 |
| 2,470,297 | 5/1949 | Fields | 604/94 X |
| 2,672,144 | 3/1954 | Cohen | 128/265 |
| 3,425,598 | 2/1969 | Kobernick | 222/83 |
| 3,802,604 | 4/1974 | Morane et al. | 222/83 |
| 4,645,487 | 2/1987 | Shishov et al. | 604/58 |
| 5,273,190 | 12/1993 | Lund | 222/83 |
| 5,284,132 | 2/1994 | Geier | 128/200.22 |
| 5,503,302 | 4/1996 | DeJonge | 222/82 |
| 5,505,336 | 4/1996 | Montgomery et al. | 222/82 |

FOREIGN PATENT DOCUMENTS

| | | | |
|---|---|---|---|
| 2020425 | 1/1991 | Canada . | |
| 528764 | 2/1993 | European Pat. Off. | 604/58 |
| 40 16 126 | 10/1991 | Germany . | |
| 81836 | 5/1953 | Norway | 604/58 |
| 147157 | 10/1954 | Sweden | 604/58 |
| 607237 | 8/1948 | United Kingdom | 604/58 |
| 1436028 | 5/1976 | United Kingdom | 604/58 |
| 1436813 | 5/1976 | United Kingdom | 604/58 |
| WO 91/06333 | 5/1991 | WIPO . | |
| WO 92/06727 | 4/1992 | WIPO . | |

*Primary Examiner*—Corrine M. McDermott
*Attorney, Agent, or Firm*—Steve T. Zelson, Esq.; James Harrington, Esq.

[57] ABSTRACT

A dispenser for dispensing a dosage or a powdery or fluid drug from a cartridge having a tubular chamber the ends of which are sealed by breakable membranes. The dispenser comprises a housing forming a cylinder which is at one end closed by an end wall through which an outlet pipe communicates with the interior of the cylinder. The other end of the cylinder is closed by a plunger which may be displaced into the cylinder. The drug cartridge is placed in a piston mounted axially displaceable in the cylinder between the end wall and the plunger, and the tubular chamber extends from one side of the piston to the other. Penetrators for breaking the membranes are provided at the inner end of the outlet pipe and the inner end of the plunger.

6 Claims, 1 Drawing Sheet

DISPOSABLE DISPENSER FOR POWDER

This application is a continuation application of application Ser. No. 07/900,027, filed Jun. 17, 1992 now abandoned.

The invention concerns a disposable dispenser for powder, and more specifically a dispenser for dispensing a dosage of a powdery drug stored in a cartridge having a tubular chamber, the ends of which are sealed by breakable membranes.

Such dispensers may be used for dispensing powdery medicine which can be absorbed through the nasal mucous membranes and which is only given occasionally, e.g. emergency administration of glucagon for treating hypoglycaemic diabetics. Therefore, the dispenser should be suited for storing an appropriate dosage of a powdery drug and should be easily operated to administer this dosage even by unprofessionals when necessary.

From U.S. Pat. No. 2,672,144 is known a disposable powder dispenser having the powdery drug stored in a bottle shaped vessel also containing a charge of compressed gas and sealed at the end of the bottle neck with a sealing which may be broken by a penetrator when the vessel is pressed into the dispenser unit. By using this dispenser care must be taken to ensure that the powder is passed up into the bottle neck—a precaution which cannot be expected to be taken by unprofessionals in an emergency situation. Further, the compressed gas may leak during storage, and consequently the dispenser may be unusable when the emergency situation occurs.

From EP 407 276 is known a dispenser having the powder stored in a tubular chamber being closed at its air inlet end by a membrane and at its outlet end by a removable lid. Immediately before use the lid is removed before the outlet end is inserted in a nostril. However, unless the powder appears as a lump wedging in the outlet, there will be a risk of spilling some of the powder, if the outlet should be inserted in the nostril of a person lying down.

A dispenser wherein the powder is stored in a tubular chamber, the ends of which are closed by penetrable membranes, is known from WO 91/06333. In this dispenser a number of chambers are successively brought into alignment with an air supply pipe and an outlet pipe and the membranes closing the chamber are penetrated by penetrators at the ends of these pipes. However, according to the construction of the apparatus the membrane at the air supply end is first broken and thereafter the membrane at the outlet is penetrated.

However, the penetrations are requested to take place in the opposite order to ensure that the outlet passage from the chamber to the nostril is opened before the chamber is opened to the pressurized air, but not until the outlet pipe is inserted in the nostril. If the membrane separating the chamber from the compartment with the pressurized air is broken first, the powder may fall out of the chamber into the compartment as an air flow through the chamber is not established until both membranes are broken.

It is the object of the invention to provide a powder dispensing device which meets the above requests without involving the stated draw-backs of the dispensers according to the known art.

This is obtained by a dispenser comprising a housing forming a cylinder which is at one end closed by an end wall through which an outlet pipe communicates with the interior of the cylinder, the other end of the cylinder being closed by a plunger which may be operated to displace it axially into the cylinder towards the end wall, the dispenser being characterized in that the powder cartridge is placed in a free piston mounted axially movably in the cylinder between the end wall and the plunger, the tubular chamber of the cartridge extending in the axial direction of the cylinder from one side of the piston to the other, and means for breaking the sealing membranes of the cartridge being provided at least at the inner end of the outlet pipe.

The operation of the dispenser according to the invention is very simple as only the plunger has to be pressed into the cylinder. The air pressure thereby provided between the plunger and the piston will force the latter forwards in the cylinder towards the end wall until the membrane facing this wall abuts the membrane breaking means provided at the inner end of the outlet tube.

The membrane breaking means may be a penetrator having a diameter smaller than the diameter of the bore of the tubular chamber and a length longer than the length of this chamber. Such a penetrator will first penetrate the membrane facing the end wall. When the piston is forced further towards the end wall of the cylinder, the penetrator will pass through the chamber and the powder to ultimately penetrate the membrane facing the plunger, this membrane being penetrated from its side facing the interior of the chamber.

According to the invention the membrane breaking means may comprise a penetrator at the mouth of the outlet tube and another penetrator at the inner end of the plunger. When the plunger is pressed into the cylinder, the magazine is by the air pressure provided pressed with its one membrane against the penetrator at the outlet pipe. When the plunger is pressed further into the cylinder the penetrator at the inner end of the plunger is pressed through the other membrane of the magazine. This embodiment ensures that the last membrane is not broken until the plunger is pressed home and the highest obtainable air pressure is provided.

To avoid that the membrane of the magazine is pressed against the penetrator at the mouth of the outlet tube during the mounting of the piston or due to an inadvertently minor push on the plunger resilient spacing means may be provided between the piston and the end wall. When a sufficient pressure is provided in the compartment between the plunger and the piston, the resilient means gives to allow the penetrator to penetrate the membrane.

The dispenser may be equipped with two outlet pipes, two chambers in the piston, and two sets of penetrators, each pipe, chamber, and penetrator set cooperating as in the monopipe solution. Thereby it is taken into account that a nostril may be blocked or may show a decreased capacity concerning assimilation of the medicine.

Figure 2:
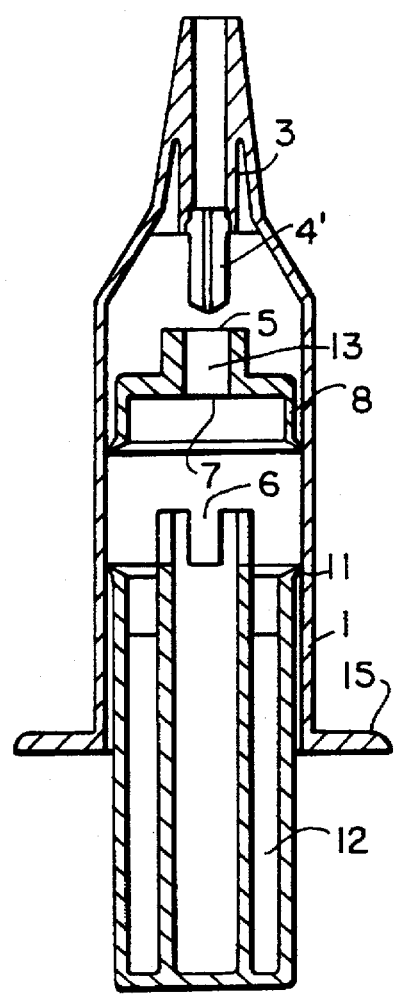

In the following the invention will be further described referring to the drawing, wherein FIG. 1 shows a sectional view of an embodiment of a powder dispenser according to the invention, and FIG. 2 shows a sectional view of another embodiment of the powder dispenser.

Figure 3:
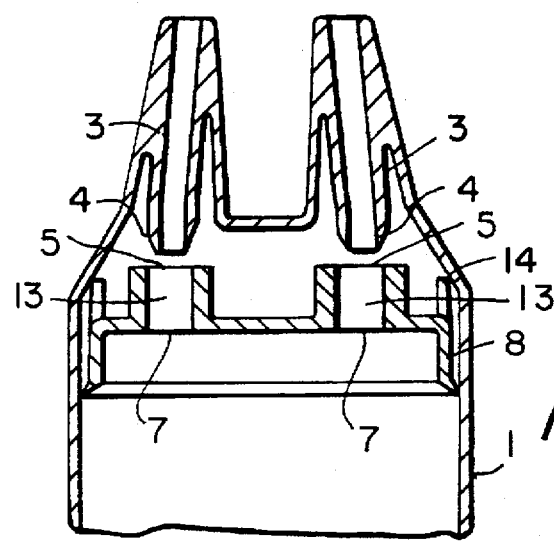

FIG. 3 shows the upper part of an embodiment of a dispenser having two outlet pipes.

An embodiment of the powder dispenser as shown in FIG. 1 comprises a housing 1 forming a cylinder which is at one end closed by an end wall through which an outlet pipe 3 communicates with the interior of the cylinder. Into the other end of the cylinder a plunger 9 is air tightly fitted forming along its perimeter a lip 11 enhancing the sealing with increasing pressure in the cylinder. The plunger is provided with an air pocket 12 to limit the maximum pressure when the plunger is pressed into the cylinder.

In the cylinder between the end wall and the plunger 9 a piston 8 is placed which is freely displaceable in the cylinder. An axial bore through the piston 8 forms a tubular chamber 13 which is at its ends closed by penetrable upper and lower membranes 5 and 7, respectively. The chamber 13 contains the powder to be dispensed.

When the plunger 9 is pressed into the cylinder the air pressure provided between the plunger 9 and the piston 8 will make the latter move axially towards the end wall.

Resilient members 14 are provided on the top of the piston 8 to keep it at some distance from the end wall and a penetrator 4 provided at the inner end of the outlet pipe 3 until the pressure at the plunger side of the piston 8 is sufficiently high to bend these resilient members, so that the upper membrane 5 is broken by the penetrator 4. The resilient members 14 are provided to ensure that the membrane 5 is not inadvertently broken by the penetrator 4 during the mounting of the piston 8 or due to minor forces exerted on the plunger 9 before the intended use of the dispenser.

After the membrane 5 has been broken due to the pressure provided under the piston 8 pressing the membrane against the penetrator 4, the pressure in the chamber will rise as the plunger 9 is pressed further into the cylinder. When the plunger is pressed home a penetrator 10 at the top of the plunger perforates the lower membrane 7 closing the chamber 13 and thereby opens for an air flow from the compartment between the plunger 9 and the piston 8 through the chamber 13 and out through the outlet pipe 3.

Whereas the penetrator 4 is designed to form a sealing around the edge of the chamber 13 when the membrane 5 has been penetrated, the penetrator 10 penetrating the membrane 7 is designed to leave passages 6 communicating the chamber 13 with the compartment between the piston 8 and the plunger 9.

At the open end of the housing 1 finger grips 15 are provided, the device being so dimensioned that the finger grips 15 may be gripped behind by the forefinger and the long finger, and the bottom of the plunger 9 may be pressed by the thumb. When the outlet pipe 3 is placed in a patient's nostril the powder may be dispensed as a small cloud into the nostril by this simple gripping and pressing operation.

In the embodiment shown in FIG. 2, all parts corresponding to the parts known from FIG. 1 are given the same reference numbers. The only difference is that the penetrator 4' is given another shape, and the penetrator 10 in FIG. 1 is omitted.

The penetrator 4' has a length exceeding the length of the chamber 13. When the piston 8 is pressed forwards in the housing 1, the upper membrane 5 is first penetrated by the penetrator 4'. This penetrator has a diameter allowing it to pass through the chamber 13 and subsequently penetrate the lower membrane 7 to open a discharge passage for the pressurized air between the piston 8 and the plunger 9. Instead of a penetrator the plunger 9 has a part 16 which may help to press the piston 8 against the penetrator 4' when the piston 8 is pressed home. This part 16 is provided with passages 6 which make space for the cutting edges of the penetrator 4' and prevent the part 16 from sealing against the lower side of the piston 8.

In the shown embodiment the penetrator 4' is a puncheon having a cross-shaped cross section and being sharpened at its front end. At its root the puncheon is provided with a means sealing along the upper edge of the chamber 13 immediately before the lower membrane 7 is punched.

It shall be noticed that the penetrators are so designed that no parts of the membranes are cut free to be entrained by the air discharged from the device. In FIG. 1 this is obtained by a recess 2 in the cutting edge of the penetrator 4 leaving a string of the membrane 5 uncut when penetrated. In FIG. 2, a cross shaped cut is made in the central part of the membrane 5 whereas the outer edge of the provided membrane sectors is still secured to the edge of the chamber.

As the assimilation capacity of the nostrils varies, it is impossible to know at forehand which nostril will be best suited for the administration of medicine. This problem may be overcome by adding medicine in both nostrils. For this purpose the dispenser in FIG. 3 has been designed. FIG. 3 shows the outlet end of the dispenser, which in this embodiment is equipped with two outlet tubes 3 each having a penetrator 4. The piston 8 has two chambers 13 aligned with the outlet tubes and the not shown plunger has penetrators correspondingly aligned with the chambers 13 and the outlet tubes 3. This alignment may be obtained by the housing 1 having a cross section which is not circular, but rather oval.

We claim:

1. A dispenser containing a dosage of a powdery drug, which can be dispensed by the dispenser, the dispenser comprising:

a housing forming a cylinder having a side wall and a first and a second end, an end wall closing the first end of the housing, a plunger closing the second end of the housing by fitting into the cylinder sealing against the side wall of the cylinder and having an inner end facing the interior of the cylinder and an outer end by which this plunger may be operated to be displaced axially into the cylinder towards the end wall of this cylinder, a first outlet pipe having a first and a second end, the first end opening through said end wall to the interior of the cylinder and the second end having a discharge opening, a piston having a from side and a rear side and a bore completely through the piston from its front side to its rear side, a first and second membrane adhered to the front and rear sides of the piston, respectively the powdery drug being confined in the bore between the first and the second sealing membranes, the piston sealing against the side wall of the cylinder and being axially displaceable in this cylinder between the end wall of the housing and the inner end of the plunger independent of this plunger, and membrane breaking means provided at least at the first end of the outlet pipe where this end opens into the cylinder.

2. A dispenser according to claim 1, wherein the membrane breaking means is provided as a cutting protrusion.

3. A dispenser according to claim 2, wherein the protrusion has a diameter smaller than the diameter of the bore of the piston and is longer than the length of this bore.

4. A dispenser according to claim 1, wherein a cutting member is provided at the inner end of the plunger, this cutting member being aligned with the bore of the piston on the rear side of this piston.

5. A dispenser according to claim 1, wherein resilient spacing means is provided between the piston and the end wall.

6. A dispenser according to claim 1, wherein a second outlet pipe is provided which outlet pipe corresponding to the first outlet pipe has a first and a second end, the first end opening through said end wall to the interior of the cylinder and the second end having a discharge opening, membrane breaking means being provided at the first end of the second outlet pipe, and a second bore being provided in the piston in which second bore drug to be discharged through the second outlet pipe is confined.

\* \* \* \* \*